US008915363B2

(12) United States Patent
Hawkes et al.

(10) Patent No.: US 8,915,363 B2
(45) Date of Patent: Dec. 23, 2014

(54) APPARATUS FOR RETAINING MEDICAL INSTRUMENTS AND RELATED METHODS (71) Applicant: Symmetry Medical Manufacturing, Inc., Warsaw, IN (US)

(72) Inventors: Jason Hawkes, Weare, NH (US); George P. Hannafin, Hudson, NH (US)

(73) Assignee: Symmetry Medical Manufacturing, Inc., Warsaw, IN (US)

(*) Notice: Subject to any disclaimer, the term of this patent is extended or adjusted under 35 U.S.C. 154(b) by 0 days.

(21) Appl. No.: 14/097,917

(22) Filed: Dec. 5, 2013

(65) Prior Publication Data
US 2014/0162207 A1 Jun. 12, 2014

Related U.S. Application Data (60) Provisional application No. 61/734,059, filed on Dec. 6, 2012.

(51) Int. Cl.
A61B 19/02 (2006.01)
A61C 19/02 (2006.01)

(52) U.S. Cl.
CPC .................... A61C 19/02 (2013.01)
USPC ............ 206/370; 206/366; 206/438; 422/300

(58) Field of Classification Search
USPC ........... 206/363–370, 438–439; 422/292, 300
See application file for complete search history.

(56) References Cited

U.S. PATENT DOCUMENTS

| | | | |
|---|---|---|---|
| 4,798,292 A | 1/1989 | Hauze | |
| 5,098,676 A | 3/1992 | Brooks, Jr. | |
| 5,372,252 A | 12/1994 | Alexander | |
| 5,490,975 A | 2/1996 | Dane | |
| 5,518,115 A | 5/1996 | Latulippe | |
| 5,525,315 A | 6/1996 | Burke | |
| 5,913,422 A | 6/1999 | Cote et al. | |
| 6,012,577 A | 1/2000 | Lewis et al. | |
| 6,099,812 A | 8/2000 | Allen et al. | |
| 7,861,860 B2 | 1/2011 | Bettenhausen et al. | |
| 8,162,138 B2 | 4/2012 | Bettenhausen et al. | |
| 2005/0161355 A1 | 7/2005 | Matthis et al. | |
| 2005/0163686 A1 | 7/2005 | Bettenhausen et al. | |
| 2006/0006087 A1 | 1/2006 | Lin | |
| 2007/0138042 A1* | 6/2007 | Wood | 206/369 |
| 2012/0094249 A1 | 4/2012 | Abene et al. | |
| 2012/0195792 A1 | 8/2012 | Duddy et al. | |

* cited by examiner

Primary Examiner — Bryon Gehman
(74) Attorney, Agent, or Firm — Hayes Soloway P.C.

(57) ABSTRACT

An apparatus and method for retaining medical instruments is disclosed. The apparatus includes a medical instrument tray having a substantially planar, rigid interior section, wherein the interior section has a plurality of holes formed therein. A flexible grommet sheet is positioned abutting a first side of the medical instrument tray, the flexible grommet sheet having a plurality of openings therein, wherein at least a portion of the plurality of openings are substantially axially aligned with the plurality of holes formed within the interior section. A substantially rigid back plate is removably attached to the medical instrument tray, wherein the flexible grommet sheet is positioned between the first side of the interior section and the back plate, and wherein the back plate has a plurality of holes positioned therein, wherein the plurality of holes are substantially axially aligned with the plurality of holes formed within the interior section.

20 Claims, 8 Drawing Sheets

| A flexible grommet sheet is positioned to abut a first side of a medical instrument tray, the medical instrument tray having substantially planar, rigid interior section, wherein the interior section has a plurality of holes formed therein, wherein the plurality of holes are substantially axially aligned with a plurality of openings within the flexible grommet sheet — 302 |

| A substantially rigid back plate is removably attached to the medical instrument tray, wherein the flexible grommet sheet is positioned between the first side of the medical instrument tray and the back plate, and wherein the back plate has a plurality of holes positioned therein, wherein the plurality of holes are substantially axially aligned with the plurality of holes formed within the medical instrument tray — 304 |

| A portion of a medical instrument is inserted through a substantially axially aligned set of at least one of the plurality of holes within the medical instrument tray, at least one of the plurality of openings within the flexible grommet sheet, and at least one of the plurality of holes within the back plate, whereby the medical instrument is retained at least partially by the flexible grommet sheet — 306 |

FIG. 14

APPARATUS FOR RETAINING MEDICAL INSTRUMENTS AND RELATED METHODS

CROSS REFERENCE TO RELATED APPLICATION

This application claims benefit of U.S. Provisional Application Ser. No. 61/734,059, entitled "Apparatus for Retaining Medical Instruments" filed Dec. 6, 2012, the entire disclosure of which is incorporated herein by reference

FIELD OF THE DISCLOSURE

The present disclosure is generally related to instrument holding devices and more particularly is related to an apparatus for retaining medical instruments and related methods.

BACKGROUND OF THE DISCLOSURE

Within the medical industry, there is a need for holding a variety of medical instruments for various purposes. For example, a surgeon needs to be able to access medical instruments for surgery quickly, a dentist needs to be able to access his or her dental tools, and virtually all medical instruments must be placed within a holder during a sterilization process. Conventional holding containers may include a variety of bases holding insertable trays that have specifically-designed areas for holding specific tools. However, with smaller tools, such as small dental tools, it is frequently inefficient to store them in these containers, since they're prone to being moved around and jostled as the container is moved. This may result in a grouping of smaller tools in one area, which means that the surgeon or medical staff member must sift through the grouping to locate a specific tool.

Conventionally, medical instruments are often held in containers or trays with holes and grommets. The grommets may be positioned within the hole and provide a secure interface between the medical instrument and the hole within the container or tray. Often, the grommets are sized to match a certain shaft size of a medical instrument, and a container or tray may include a variety of different sized grommets, each specifically engineered and designed to hold one of a variety of medical instruments. These medical instruments have varying shaft sizes and it often becomes tedious to search for the appropriately sized grommet that matches a particular shaft size of the medical instrument. It is not uncommon for a medical tray to have fifty or more grommets, with a dozen or more different sizes. Thus, matching a specific medical instrument to a specifically sized grommet may be a timely and inefficient process.

Most grommets in use today are intended to be permanent fixtures in medical sterilization trays, in that they are not designed to be removed on a regular basis. This is due to the high risk of harboring bacteria and other contaminants within the spaces, crevices and other areas exposed when the grommet is removed from the tray. When the grommets are permanently installed within the holes, the surfaces of the grommets form tight seals with the container or the tray. This seal may often prevent bacterial from becoming lodge within cracks, crevices or other areas, but it is susceptible to some bacterial contamination, especially when users remove the grommets from the tray. When removed from the tray, grommets may become damaged, which may lead to failing seals and additional places for bacteria to be harbored.

Thus, a heretofore unaddressed need exists in the industry to address the aforementioned deficiencies and inadequacies.

SUMMARY OF THE DISCLOSURE

Embodiments of the present disclosure provide an apparatus for retaining medical instruments. Briefly described, in architecture, one embodiment of the apparatus, among others, can be implemented as follows. A medical instrument tray has substantially planar, rigid interior section, wherein the interior section has a plurality of holes formed therein. A flexible grommet sheet is positioned abutting a first side of the medical instrument tray, the flexible grommet sheet having a plurality of openings therein, wherein at least a portion of the plurality of openings are substantially axially aligned with the plurality of holes formed within the interior section. A substantially rigid back plate is removably attached to the medical instrument tray, wherein the flexible grommet sheet is positioned between the first side of the interior section and the back plate, and wherein the back plate has a plurality of holes positioned therein, wherein the plurality of holes are substantially axially aligned with the plurality of holes formed within the interior section.

The present disclosure can also be viewed as providing a system for retaining a medical instrument. Briefly described, in architecture, one embodiment of the system, among others, can be implemented as follows. A medical instrument tray has substantially planar, rigid interior section and a plurality of sidewalls extending substantially perpendicularly from the interior section, wherein the interior section has a plurality of holes formed therein. An entirely flexible grommet sheet is positioned abutting a first side of the medical instrument tray, the flexible grommet sheet having a plurality of openings therein, wherein at least a portion of the plurality of openings are substantially axially aligned with the plurality of holes formed within the interior section. A substantially rigid back plate is removably attached to the medical instrument tray, wherein the flexible grommet sheet is positioned between the first side of the interior section and the back plate, wherein the grommet sheet is tensionedly stretched across the back plate, and wherein the back plate has a plurality of holes positioned therein, wherein the plurality of holes are substantially axially aligned with the plurality of holes formed within the interior section.

The present disclosure can also be viewed as providing a method of retaining medical instruments within a medical instrument container. In this regard, one embodiment of such a method, among others, can be broadly summarized by the following steps: positioning a flexible grommet sheet to abut a first side of a medical instrument tray, the medical instrument tray having substantially planar, rigid interior section, wherein the interior section has a plurality of holes formed therein, wherein the plurality of holes are substantially axially aligned with a plurality of openings within the flexible grommet sheet; removably attaching a substantially rigid back plate to the medical instrument tray, wherein the flexible grommet sheet is positioned between the first side of the medical instrument tray and the back plate, and wherein the back plate has a plurality of holes positioned therein, wherein the plurality of holes are substantially axially aligned with the plurality of holes formed within the medical instrument tray; and inserting a portion of a medical instrument through a substantially axially aligned set of at least one of the plurality of holes within the medical instrument tray, at least one of the plurality of openings within the flexible grommet sheet, and at least one of the plurality of holes within the back plate, whereby the medical instrument is retained at least partially by the flexible grommet sheet.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
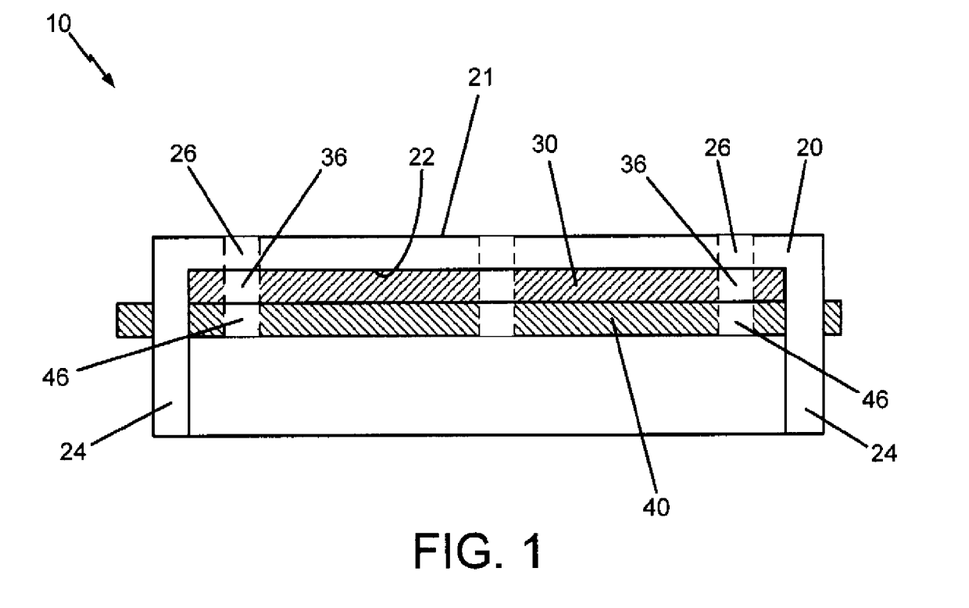
FIG. 1 is a side cross-sectional view illustration of an apparatus for retaining medical instruments, in accordance with a first exemplary embodiment of the present disclosure.

FIG. 1 is a side cross-sectional view illustration of an apparatus for retaining medical instruments 10, in accordance with a first exemplary embodiment of the present disclosure. The apparatus for retaining medical instruments 10, which may be referred to as 'apparatus 10,' includes a medical instrument tray 20 having a substantially planar, rigid interior section 21, wherein the interior section 21 has a plurality of holes 26 formed therein. A flexible grommet sheet 30 is positioned abutting a first side 22 of the medical instrument tray 20. The flexible grommet sheet 30 has a plurality of openings 36 therein, wherein at least a portion of the plurality of openings 36 are substantially axially aligned with the plurality of holes 26 formed within the interior section 21. A substantially rigid back plate 40 is removably attached to the medical instrument tray 20, wherein the flexible grommet sheet 30 is positioned between the first side 22 of the medical instrument tray 20 and the back plate 40, and wherein the back plate 40 has a plurality of holes 46 positioned therein, wherein the plurality of holes 46 are substantially axially aligned with the plurality of holes 26 formed within the interior section 21.

The apparatus 10 may be used for holding different types of instruments, namely medical instruments used for medical procedures, operations, and surgeries. For example, the apparatus 10 may be used to hold medical instruments in surgical environments before, during and/or after a surgical procedure, or a medical instrument sterilization process. Similarly, the apparatus 10 may be used with dental instruments for dental operations, routine cleanings, or for any other use. Other settings and uses within the medical field are also envisioned, all of which are considered within the scope of the present disclosure.

The medical instrument tray 20, which may be referred to simply as the tray 20 throughout this disclosure may have a substantially planar, rigid interior portion 21, which is generally positioned within the middle of the tray 20. The substantially planar, rigid interior portion may have any number of holes 26 positioned therein. The tray 20 may have some curvatures or structure features, such as different heights, all of which are considered within the scope of the disclosure, but the interior portion 21 may generally be substantially planar with little or no curvatures. The tray 20 includes at least a first side 22, which may form one side of the substantially planar structure of the interior portion 21. As is shown in FIG. 1, the first side 22 is positioned along the interior or underside of the top surface of the interior portion 21.

The tray may be substantially rigid in that it can hold a shape and support a quantity of medical instruments therein. For example, it may be common for the tray 20 to be formed from aluminum or other rigid metals, plastics, or polymers. The tray 20 may often be used in concert with a medical instrument sterilization container having a base and a cover and any number of other features, as discussed relative to FIGS. 11-13, all of which are considered within the scope of the present disclosure. The tray 20 may have a plurality of sidewalls 24 extending in a substantially perpendicular from the interior section 21, which may be used to position the tray 20 a predetermined height off of the bottom of the medical instrument sterilization container or similar structure, such as a surgical table. For example, the plurality of sidewalls 24 may extend from the interior section 21 beyond the rigid back plate 40.

The flexible grommet sheet 30 may be constructed all or in part from medical-grade silicone materials or similar materials, which are known in the art. Medical-grade silicone may be capable of withstanding the conditions present in autoclaves and other sterilization devices, including high temperatures, steam, sterilization chemicals, or other sterilization treatments. The grommet sheet 30 may be partially or entirely flexible, such that it can be stretched, tensioned, or otherwise biasly connected to other components of the apparatus 10. The flexible grommet sheet 30 may be substantially planar and have a footprint that substantially corresponds to the length and width dimensions of the interior section 21 of the tray 20, such that the flexible grommet sheet 30 can be properly placed proximate to the interior section 21. The flexible grommet sheet 30 is positioned abutting the first side 22 of the interior section 21, which may include having the flexible grommet sheet 30 directly abutting the first side 22 of the interior section 21.

The flexible grommet sheet 30 has a plurality of openings 36 therein which are positioned to substantially align with the holes 26 of the interior section 21. For example, the openings 36 may precisely match the holes 26 of the interior section 21 such that each opening 36 of the flexible grommet sheet 30 is substantially axially aligned with a hole 26 of the interior section 21. Alignment may be perfect or imperfect, since the flexible nature of the flexible grommet sheet 30 may provide for imperfect dimensions and positions. In another example, the flexible grommet sheet 30 may have many openings 36 that are positioned throughout the flexible grommet sheet 30 in a pattern, such that when the flexible grommet sheet 30 is positioned proximate to the interior section 21, only a portion of the openings 36 axially align with the holes 26 of the tray 20. It is noted that the openings 36 of the flexible grommet sheet 30 may have any shape or size, including substantially circular openings, oval openings, linear openings, intersecting linear openings, star-shaped openings, and grid-like openings, in addition to other shaped openings not specifically mentioned herein.

The rigid back plate 40 may be formed from any substantially rigid material, such as aluminum, metals, or rigid plastics. The back plate 40 may be a thin structure with a footprint that substantially matches that of the flexible grommet sheet 30. The back plate 40 may be removably attachable to the tray 20 with a number ways. For example, the back plate 40 may have a shape or feature that engages with the tray 20 or a sidewall 24 of the tray 20, such that the back plate 40 can be held in a substantially stationary position relative to the tray 20. Connections between the back plate 40 and the tray 20 are described further relative to FIGS. 4-10.

When the apparatus 10 is assembled, the flexible grommet sheet 30 is positioned between the first side 22 of the interior section 21 and the back plate 40. In this position, the back plate 40 may retain the flexible grommet sheet 30 in a substantially stationary position, due to the friction between the flexible grommet sheet 30 contacting the first side 22 of the interior section 21 and the back plate 40. It may be preferable for the back plate 40 be positioned close enough to the first side 22 of the interior section 21 such that the flexible grommet sheet 30 is directly sandwiched and/or biased between the back plate 40 and the tray 20.

Any number of holes 46 may be included within the back plate 40, all of which may substantially correspond and be axially aligned with holes 26 of the interior section 21. When the apparatus 10 is assembled, the holes 26 of the interior section 21 may be in alignment with the holes 46 of the back plate 40 as well as at least a portion of the openings 36 of the flexible grommet sheet 30. This configuration allows for a medical instrument to be inserted through a hole 26 of the interior section 21, an opening 36 of the flexible grommet sheet 30, and a hole 46 of the back plate 40. When the medical instrument is inserted into these holes 26, 46 and openings 36, it may be retained in place within the apparatus 10 such that it can be processed through a sterilization process or stored for later use.

Figure 2:
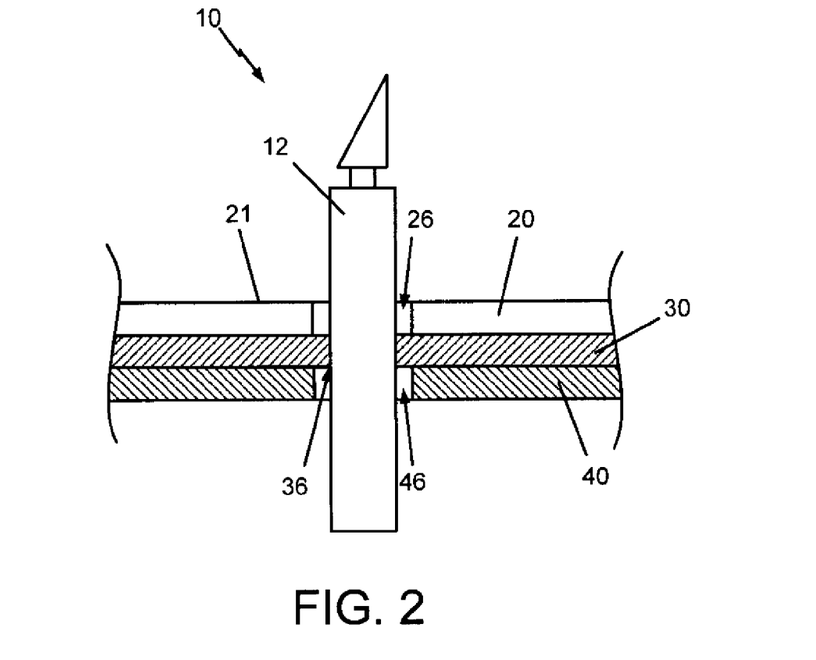
FIG. 2 is a side cross-sectional view illustration of the apparatus for retaining medical instruments of FIG. 1 in use with a medical instrument, in accordance with the first exemplary embodiment of the present disclosure.

FIG. 2 is a side cross-sectional view illustration of the apparatus 10 for retaining medical instruments of FIG. 1 with a medical instrument 12, in accordance with the first exemplary embodiment of the present disclosure. As is shown in FIG. 2, a medical instrument 12 may be retained successfully within the apparatus 10 by being frictionally contacted by the flexible grommet sheet 30. The openings 36 of the flexible grommet sheet 30 may be sized smaller than the holes 26 of the interior section 21 and the holes 46 of the back plate 40. When the holes 26, 46 and openings 36 are aligned, the medical instrument 12 positioned therein may be contacted by the flexible grommet sheet 30, in particular, the portions of the flexible grommet sheet 30 that define the openings 36. While the medical instrument 12 may contact the tray 20 or back plate 40, these structures may generally have low frictional properties to assist with retaining the medical instrument 12.

The apparatus 10 may have holes 26, 46 and openings 36, in the interior section 21, back plate 40, and the flexible grommet sheet 30, respectively, that are sized the same or differently. For example, these holes 26, 46 and openings 36 may have varying sizes to accommodate medical instruments 12 with different dimensions. In another example, these holes 26, 46 and openings 36 may have uniform sizes yet still be capable of retaining medical instruments 12 having different dimensions. When the openings 36 of the flexible grommet sheet 30 are sized smaller than the holes 26, 46 of the interior section 21 and back plate 40, the portions of the flexible grommet sheet 30 forming the openings 36 may be biased away from the center axis of the opening 36 to varying degrees, thereby allowing for varying sized medical instruments 12 to be positioned therein. There may be sufficient clearance between the medical instrument 12 and the tray 20 and back plate 40 such that during a sterilization process, sterilization materials fully and properly sterilize the medical instrument 12.

Figure 3:
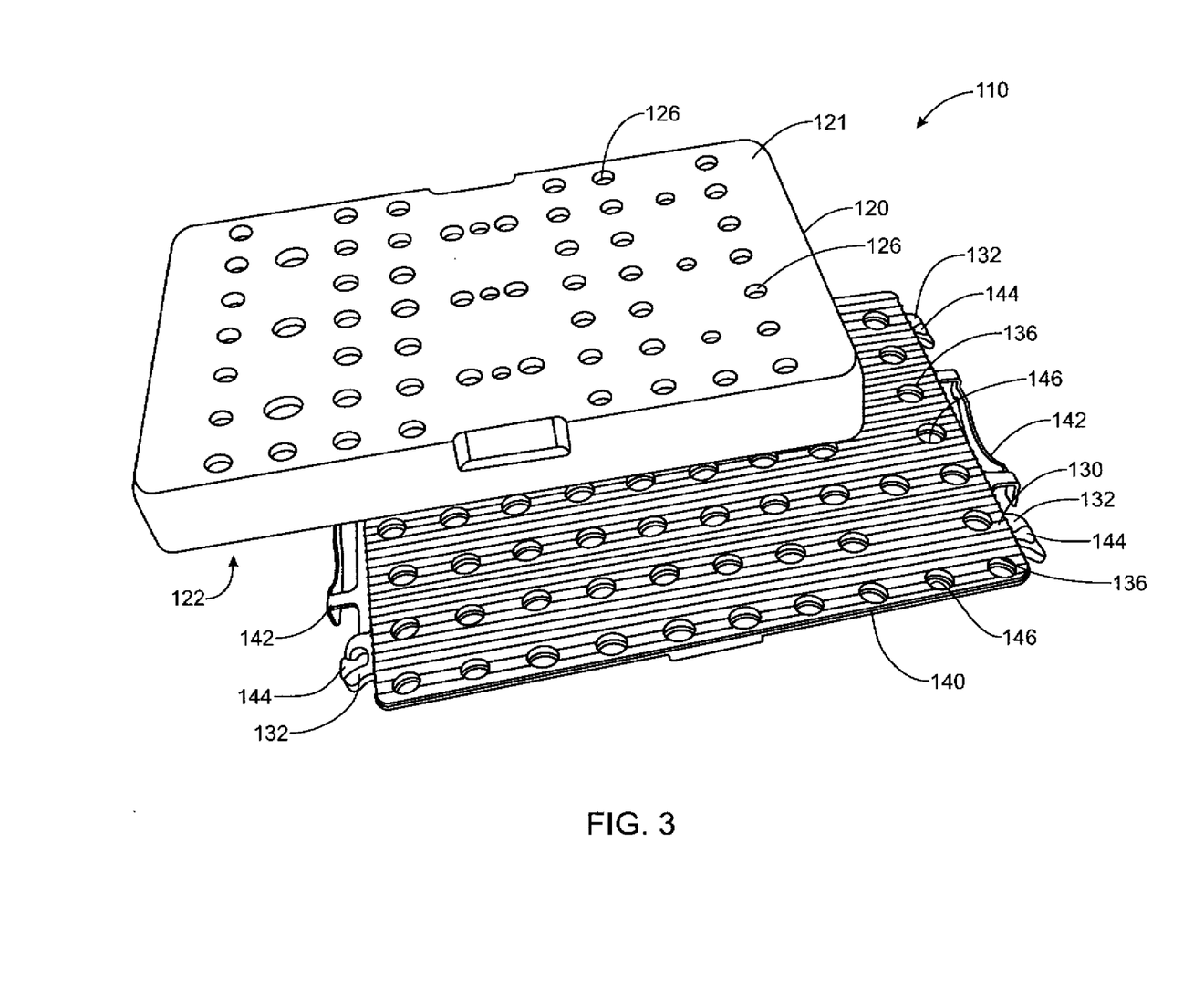
FIG. 3 is a partially unassembled plan view illustration of the apparatus for retaining medical instruments, in accordance with a second exemplary embodiment of the present disclosure.

FIG. 3 is a partially unassembled plan view illustration of the apparatus for retaining medical instruments 110, in accordance with a second exemplary embodiment of the present disclosure. The apparatus for retaining medical instruments 110, which may be referred to as 'apparatus 110,' may be substantially similar other embodiments of this disclosure and include any of the structures, components, or functions thereof. The apparatus 110 includes a medical instrument tray 120 having a substantially planar, rigid interior section 121, wherein the interior section 121 has a plurality of holes 126 formed therein. A flexible grommet sheet 130 is positioned abutting a first side 122 of the medical instrument tray 120. The flexible grommet sheet 130 has a plurality of openings 136 therein, wherein at least a portion of the plurality of openings 136 are substantially axially aligned with the plurality of holes 126 formed within the interior section 121. A substantially rigid back plate 140 is removably attached to the medical instrument tray 120, wherein the flexible grommet sheet 130 is positioned between the first side 122 of the medical instrument tray 120 and the back plate 140, and wherein the back plate 140 has a plurality of holes 146 positioned therein, wherein the plurality of holes 146 are substantially axially aligned with the plurality of holes 126 formed within the interior section 121.

As is shown in FIG. 3, the flexible grommet sheet 130 may be affixed to the back plate 140 with an opening functioning as an attaching structure 132, e.g., loops of flexible material, which engage with protrusions or male fastener structures 144 of the back plate 140. The male fastener structures 144 may extend from a peripheral of the rigid back plate 142 and the attaching structures 132 may be positioned on the male fastener structure 144. Four or more male fastener structures 144 may be included to hold the flexible grommet sheet 130 at four or more points along its edges. As is shown in FIG. 3, each of the four male fastener structures 144 are located at approximate corners of the back plate 140 and each of the four attaching structures 132 of the flexible grommet sheet 130 are positioned at approximate corners thereof.

The back plate 140 and flexible grommet sheet 130 may be repeatedly removably attached to the tray 120. If and/or when the apparatus 110 becomes dirty or unsterile, the tray 120, flexible grommet sheet 130, and back plate 140 may be separated from one another and cleaned appropriately. During use, the close abutment of the back plate 140 to the flexible grommet sheet 130 and the tray 120 may prevent bacteria and other harmful contaminants from becoming lodged or being harbored between the flexible grommet sheet 130 and the tray 120 or the back plate 140. By decreasing the available areas for bacterial contamination of the sterilization device, the apparatus 110 offers a safer means of sterilization over conventional medical instrument sterilization devices.

Figure 4:
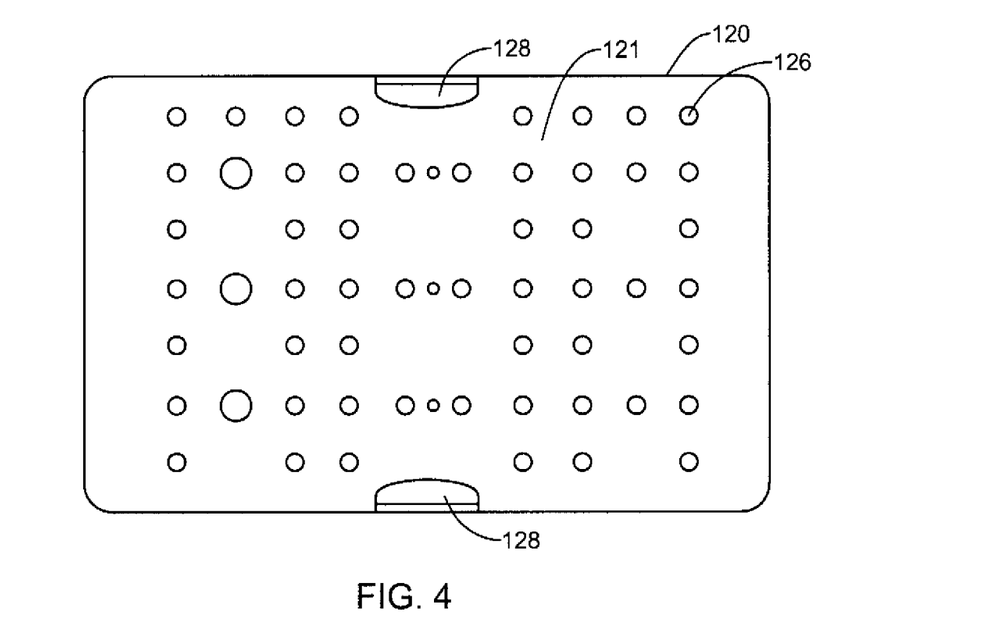
FIG. 4 is a top view illustration of the medical instrument tray of the apparatus for retaining medical instruments of FIG. 3, in accordance with the second exemplary embodiment of the present disclosure.

FIG. 4 is a top view illustration of the medical instrument tray 120 of the apparatus for retaining medical instruments 110 of FIG. 3, in accordance with the second exemplary embodiment of the present disclosure. As is shown in FIG. 4, the interior section 121 of the tray 120 may be substantially formed in the middle of the tray 120, whereby the edges of the tray 120 terminate into the sidewalls that extend away from the interior section 121. Any number of holes 126 may be formed within the interior section 121 and the holes may have varying sizes. Portions of the interior section 121 may also be without holes. The tray 120 may include one or more slots 128 which are formed on the edges of the tray 120. The slots 128 may be openings within the tray 120 that allow engagement with tabs on the side of the back plate (FIG. 7).

Figure 5:
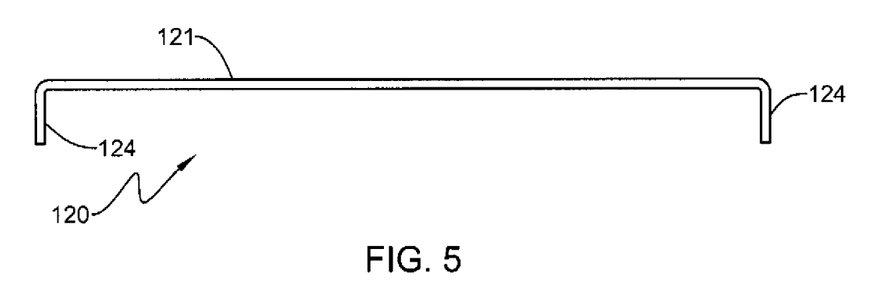
FIG. 5 is a side cross-sectional view illustration of the medical instrument tray of the apparatus for retaining medical instruments of FIG. 4, in accordance with the second exemplary embodiment of the present disclosure.
Figure 6:
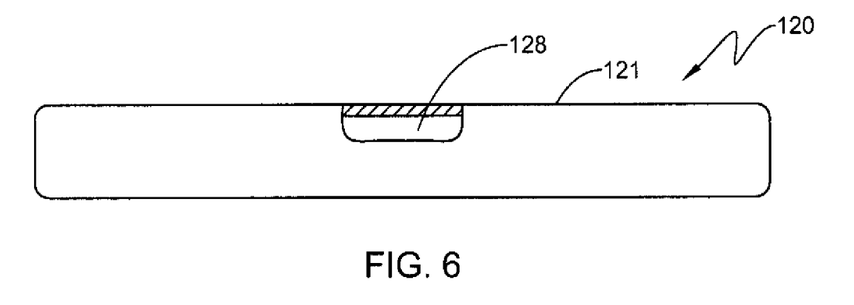
FIG. 6 is a side view illustration of the medical instrument tray of the apparatus for retaining medical instruments of FIG. 4, in accordance with the second exemplary embodiment of the present disclosure.

FIG. 5 is a side cross-sectional view illustration of the medical instrument tray of the apparatus for retaining medical instruments of FIG. 4, in accordance with the second exemplary embodiment of the present disclosure. FIG. 6 is a side view illustration of the medical instrument tray of the apparatus for retaining medical instruments of FIG. 4, in accordance with the second exemplary embodiment of the present disclosure. Relative to FIGS. 4-6, the slots 128 within the tray 120 may be formed within the corner of the tray 120, in an area positioned between the sidewalls 124 and the edge of the interior section 121 of the tray. Having the slots 128 positioned within the corners may allow for more convenient insertion of the tabs of the back plate into the slots 128, thereby allowing easy insertion and removal of the back plate from the tray 120.

Figure 7:
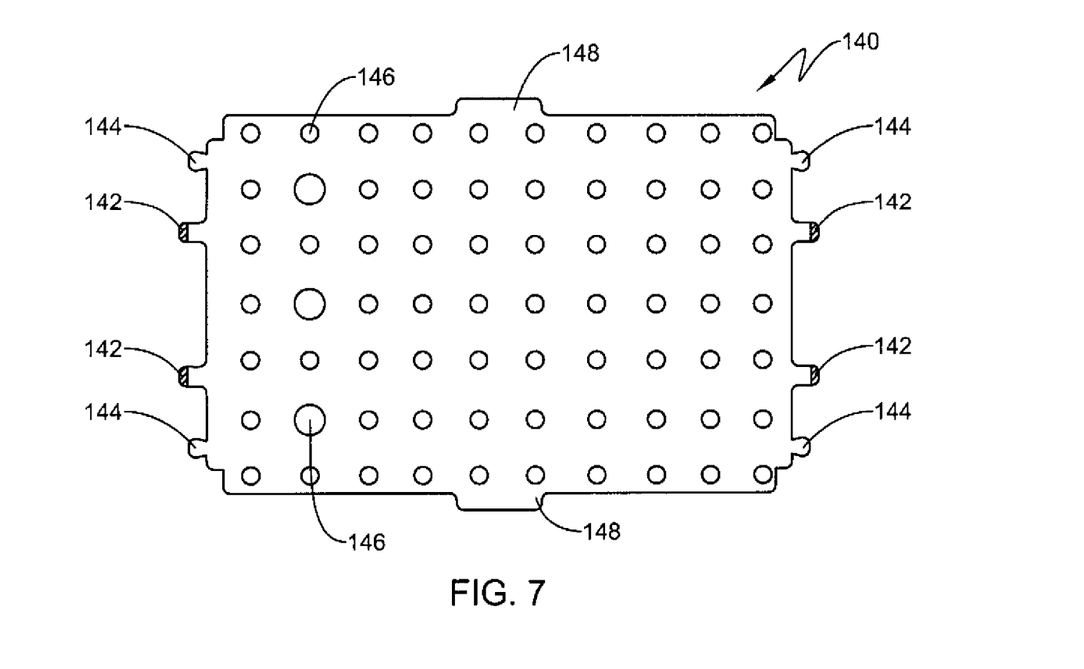
FIG. 7 is a top view illustration of the back plate of the apparatus for retaining medical instruments of FIG. 3, in accordance with the second exemplary embodiment of the present disclosure.

FIG. 7 is a top view illustration of the back plate 140 of the apparatus for retaining medical instruments 110 of FIG. 3, in accordance with the second exemplary embodiment of the present disclosure. As described relative to FIG. 3, the male fastener structures 144 positioned on the back plate 140 and used for connecting the grommet sheet to the back plate 140 may include at least two male fastener structures 144 positioned on opposing edges of the rigid back plate 140. The plurality of attaching structures 132 (FIG. 3) of the flexible grommet sheet may be connected on each of the male fastener structures 144, and the grommet sheet may be biasedly tensioned between the attaching structures 132 on opposing sides.

Also shown in FIG. 7 are the tabs 148 positioned on peripheral edges of the back plate 140. The tabs 148 may be engaged with the slots 128 of the tray 120 (FIGS. 3-6). The tabs 148 may include a variety of sizes and shapes, including shapes with rounded edges to lessen scratching the tray 120 when the back plate 140 is being engaged with the tray 120. When the back plate 140 is being engaged with the tray 120, the back plate 140 may be forcefully deformed from a substantially planar shape, thereby allowing the tabs 148 to move closed together. Relative to FIGS. 3-7, this forceful deformation of the back plate 140 may allow the tabs 148 to be moved past the sidewalls 122 of the tray 120 and into the slots 128 where the tabs 148 may be expanded outwards to their non-biased position. In this manner, the back plate 140 may be removably attached to the tray 120 by use of the tabs 148 and the slots 128. The back plate 140 may also include a slight curvature to allow for a natural bias towards the tray 120 when the back plate 140 is engaged with the tray 120. This slight curvature may assist with frictionally securing the grommet sheet 130 between the back plate 140 and the tray 120.

Figure 8:
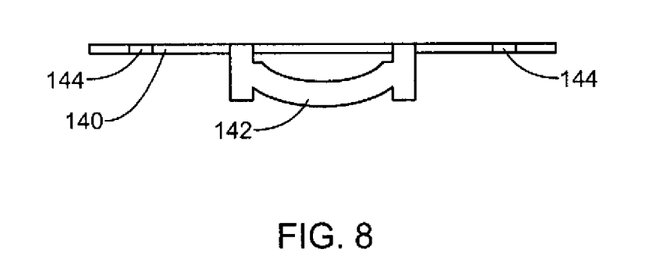
FIG. 8 is a side view illustration of the back plate of the apparatus for retaining medical instruments of FIG. 7, in accordance with the second exemplary embodiment of the present disclosure.

FIG. 8 is a side view illustration of the back plate 140 of the apparatus for retaining medical instruments 110 of FIG. 7, in accordance with the second exemplary embodiment of the present disclosure. The back plate 140 may include handles 142 formed thereon which may be used to move and/or configure the back plate 140, as well as to affix the back plate 140 to the tray 120 in certain situations. The handles 142 may extend substantially perpendicular from substantially planar back plate 140. The handles 142 may be positioned between the male fastener structures 144 and they may have any shape, such as one with an opening within the handle 142. When the back plate 140 is engaged with the tray 120, the handles 142 may be positioned substantially parallel and abutting the sidewalls 124 of the tray 120 (FIGS. 3-6).

Figure 9:
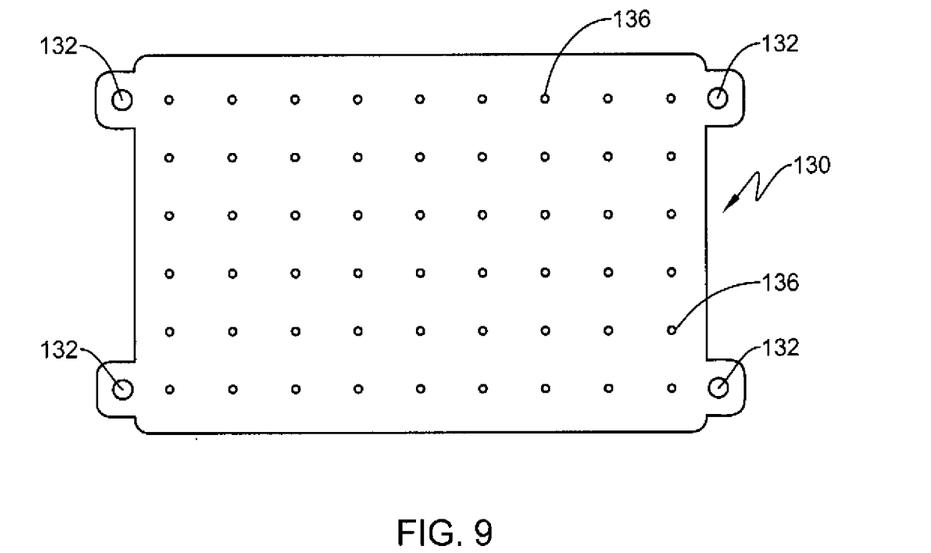
FIG. 9 is a top view illustration of the flexible grommet sheet of the apparatus for retaining medical instruments of FIG. 3, in accordance with the second exemplary embodiment of the present disclosure.
Figure 10:
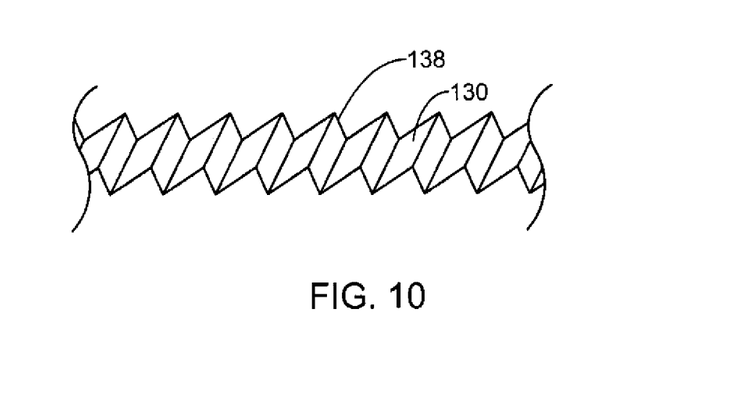
FIG. 10 is a side cross-sectional view illustration of the flexible grommet sheet of the apparatus for retaining medical instruments of FIG. 9, in accordance with the second exemplary embodiment of the present disclosure.

FIG. 9 is a top view illustration of the flexible grommet sheet 130 of the apparatus for retaining medical instruments 110 of FIG. 3, in accordance with the second exemplary embodiment of the present disclosure. FIG. 10 is a side cross-sectional view illustration of the flexible grommet sheet 130 of the apparatus for retaining medical instruments 110 of FIG. 9, in accordance with the second exemplary embodiment of the present disclosure. Relative to FIG. 9, the attaching structures 132 of the flexible grommet sheet 130 may be positioned on the edges of the grommet sheet 130, substantially in a position that corresponds to the male fastener structures 144 of the back plate 140 (FIGS. 7-8). Relative to FIG. 10, the grommet sheet 130 may include a textured surface 138 thereon, which may include ridges or other texturing. The textured surface 138 may be useful in retaining medical instruments, preventing glare and light reflection, and increasing durability of the grommet sheet 130, as well as provide other benefits.

Figure 11:
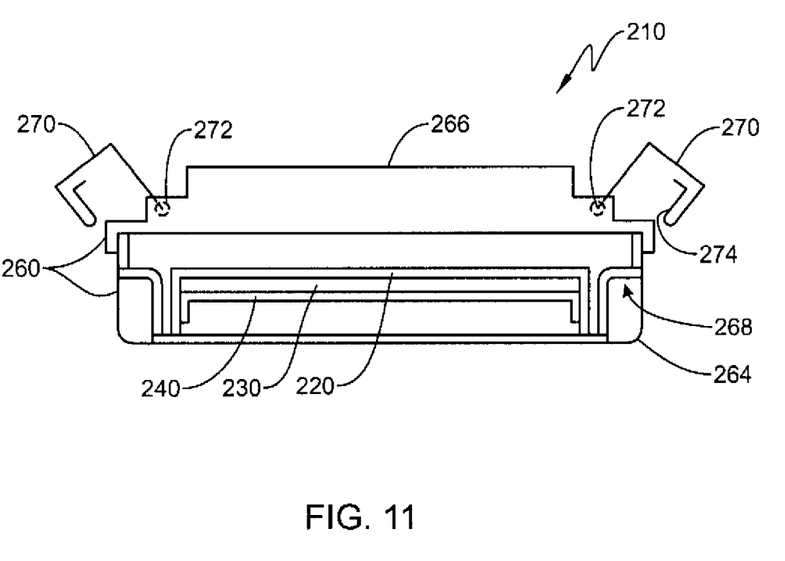
FIG. 11 is a side cross-sectional view illustration of an apparatus for retaining medical instruments with an outer case, in accordance with a third exemplary embodiment of the present disclosure.
Figure 12:
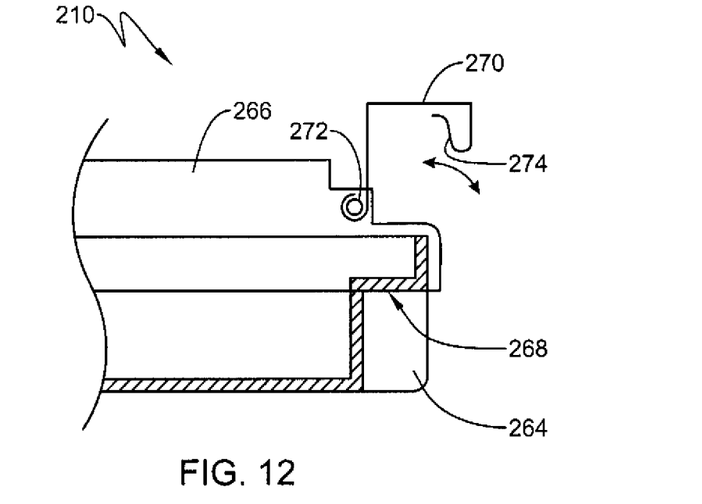
FIG. 12 is a side cross-sectional view illustration of the apparatus for retaining medical instruments with the outer case and a fastener in an unlocked position, in accordance with the third exemplary embodiment of the present disclosure.
Figure 13:
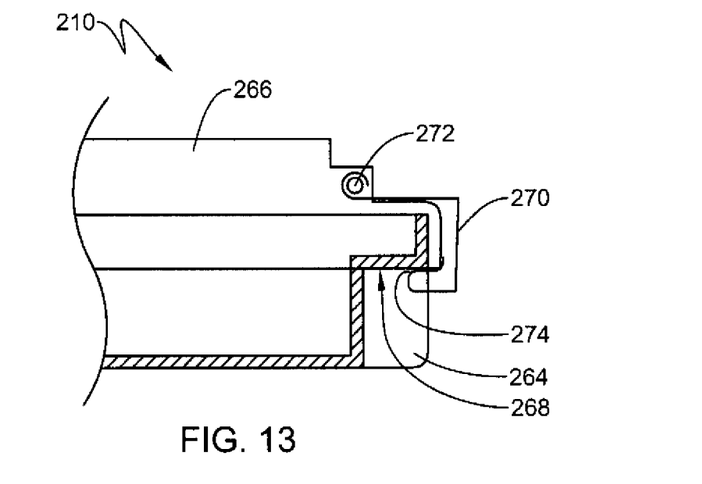
FIG. 13 is a side cross-sectional view illustration of the apparatus for retaining medical instruments with the outer case and a fastener in a locked position, in accordance with the third exemplary embodiment of the present disclosure.

FIG. 11 is a side cross-sectional view illustration of an apparatus for retaining medical instruments 210 with an outer case 260, in accordance with a third exemplary embodiment of the present disclosure. FIG. 12 is a side cross-sectional view illustration of the apparatus for retaining medical instruments 210 with the outer case 260 and a fastener 270 in an unlocked position, in accordance with the third exemplary embodiment of the present disclosure. FIG. 13 is a side cross-sectional view illustration of the apparatus for retaining medical instruments 210 with the outer case 260 and a fastener 270 in a locked position, in accordance with the third exemplary embodiment of the present disclosure. The apparatus for retaining medical instruments 210, which may be referred to herein simply as 'apparatus 210' may be substantially similar other embodiments of this disclosure and include any of the structures, components, or functions thereof.

As is shown in FIG. 11, the apparatus 210, generally having the tray 220, the flexible grommet sheet 230, and the back plate 240, may be entirely positioned within the outer case 260. The outer case 260 may have an interior compartment 262, and the tray 220, the flexible grommet sheet 230, and the back plate 240 may be removably locatable within the interior compartment 262. The outer case 260 may include a base 264, a cover 266, and at least one fastener 270 movably connected to one of the base 264 and the cover 266. The fastener 270 may be movable between a locked position (FIG. 13) and an unlocked position (FIG. 12). The base 264 and the cover 266 may be structures formed from materials conventionally used within medical sterilization, such that the base 264 and the cover 266 can withstand the conditions associated with sterilizing environments. The interior compartment 262 formed between the base 264 and the cover 266 may be sized to receive the combined tray 220, grommet sheet 230, and back plate 240 in an assembled configuration.

The cover 266 may be sized to fit on the base 264 whereby the fasteners 270 may retain the cover 266 to the base 264. The fastener 270 may be pivotally connected to the cover 266 with an axle 272 that is connected between at least two portions of the cover 266. The fastener 270 may pivot between an unlocked position (FIG. 12) and a locked position (FIG. 13). In the locked position, the distal end of the fastener 270 may be biasedly engaged with a recessed portion 268 of the base 264. The fastener 270 may include a biased fastener, such as a bent clip constructed from plastic or metal that is capable of being biased around a portion of the base 264. The fastener 270 may have a shape with various angles to allow portions of the fastener 270 to be biased, such as by being compressed and expanding from a natural state. For example, the biased fastener 270 may include at least one contact structure 274 positioned to contact the recessed portion 268 of the base 264 when in the locked position (FIG. 13). Frictional contact between the contact structure 274 and the recessed portion 268 may secure the fasteners 270 in the locked position, thereby retaining the cover 266 to the base 264.

Figure 14:
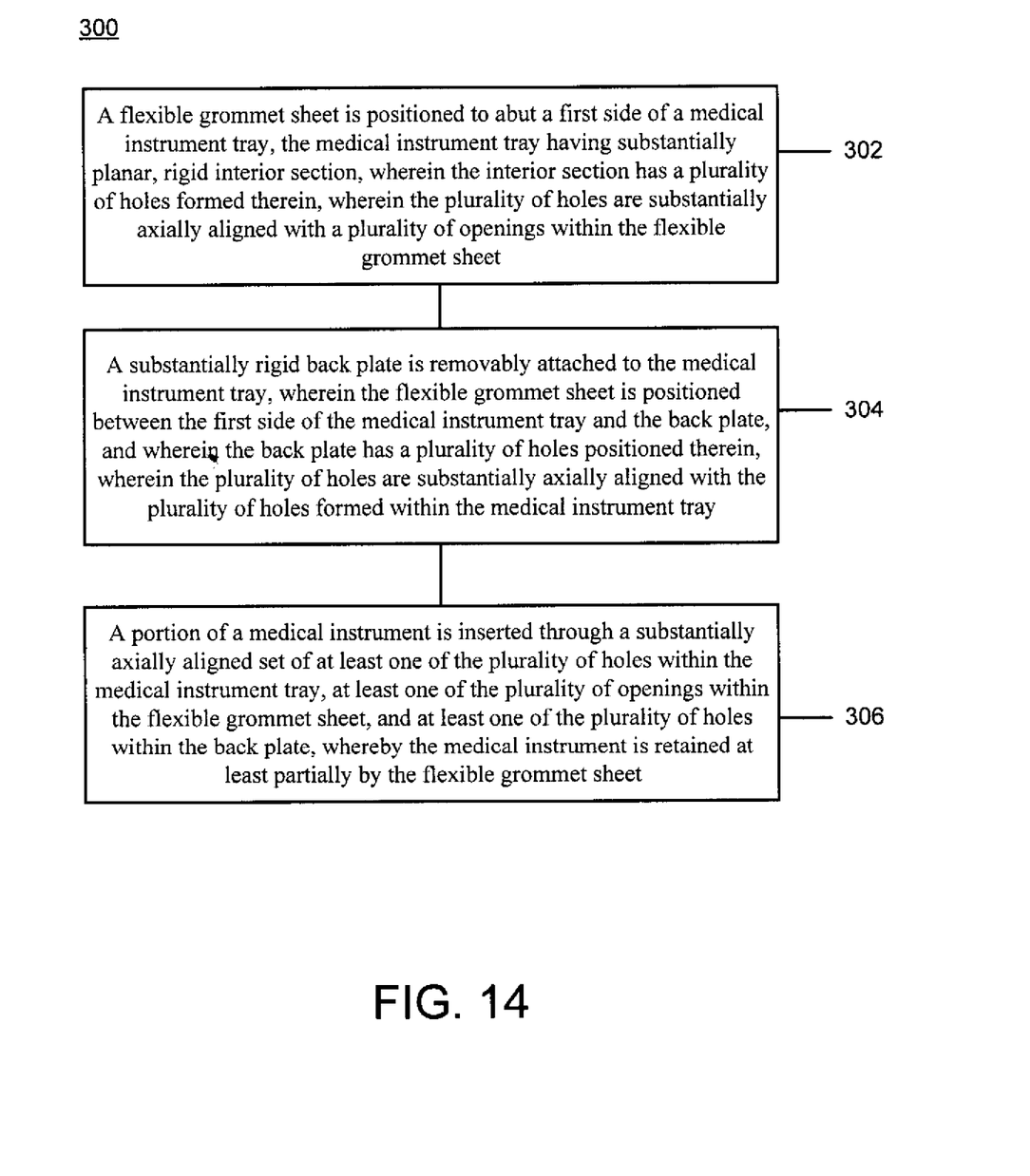
FIG. 14 is a flowchart illustrating a method of retaining medical instruments within a medical instrument container, in accordance with a fourth exemplary embodiment of the present disclosure.

FIG. 14 is a flowchart 300 illustrating a method of retaining medical instruments within a medical instrument container, in accordance with a fourth exemplary embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 302, a flexible grommet sheet is positioned to abut a first side of a medical instrument tray, the medical instrument tray having substantially planar, rigid interior section, wherein the interior section has a plurality of holes formed therein, wherein the plurality of holes are substantially axially aligned with a plurality of openings within the flexible grommet sheet. A substantially rigid back plate is removably attached to the medical instrument tray, wherein the flexible grommet sheet is positioned between the first side of the medical instrument tray and the back plate, and wherein the back plate has a plurality of holes positioned therein, wherein the plurality of holes are substantially axially aligned with the plurality of holes formed within the medical instrument tray (block 304). A portion of a medical instrument is inserted through a substantially axially aligned set of at least one of the plurality of holes within the medical instrument tray, at least one of the plurality of openings within the flexible grommet sheet, and at least one of the plurality of holes within the back plate, whereby the medical instrument is retained at least partially by the flexible grommet sheet (block 306). The method may include any additional number of steps, processes, or functions, including any disclosed relative to FIGS. 1-13.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

What is claimed is:

1. An apparatus for retaining medical instruments comprising:
   a medical instrument tray having a substantially planar, rigid interior section, wherein the interior section has a plurality of holes formed therein;
   a flexible grommet sheet positioned abutting a first side of the medical instrument tray, the flexible grommet sheet comprising a flexible material formed into a substantially planar sheet having a plurality of openings therein, at least two openings of the plurality of openings acting in the manner of a grommet sized to receive a medical instrument, wherein at least a portion of the plurality of openings are substantially axially aligned with the plurality of holes formed within the interior section; and
   a substantially rigid back plate removably attached to the medical instrument tray, wherein the flexible grommet sheet is positioned between the first side of the interior section and the back plate, and wherein the back plate has a plurality of holes positioned therein, wherein the plurality of holes are substantially axially aligned with the plurality of holes formed within the interior section.

2. The apparatus for retaining medical instruments of claim 1, wherein the flexible grommet sheet is directly sandwiched between the first side of the interior section and the back plate.

3. The apparatus for retaining medical instruments of claim 1, wherein the flexible grommet sheet is biased between the first side of the interior section and the back plate.

4. The apparatus for retaining medical instruments of claim 1, wherein at least one width dimension of an opening of the plurality of openings of the flexible grommet sheet is smaller than a diameter of a hole of the plurality of holes within the interior section and the back plate.

5. The apparatus for retaining medical instruments of claim 1, wherein the medical instrument tray further comprises a plurality of sidewalls extending from the interior section, wherein the plurality of sidewalls extend beyond the rigid back plate.

6. The apparatus for retaining medical instruments of claim 1, wherein the flexible grommet sheet has a textured surface.

7. The apparatus for retaining medical instruments of claim 1, wherein the rigid back plate further comprises at least one male fastener structure extending from a peripheral of the rigid back plate, wherein at least one of the plurality of openings in the flexible grommet sheet are positionable on the male fastener structure.

8. The apparatus for retaining medical instruments of claim 7, wherein the at least one male fastener structure further comprises at least two male fastener structures positioned on opposing edges of the rigid back plate, wherein a first of the plurality of openings of the flexible grommet sheet positioned on a first of the at least two male fastener structures, and a second of the plurality of openings of the flexible grommet sheet is positioned on a second of the at least two male fastener structures, wherein the flexible grommet sheet is tensioned between the first and second openings of the flexible grommet sheet.

9. The apparatus for retaining medical instruments of claim 1, further comprising at least one tab formed on an edge of the rigid back plate, wherein the at least one tab is received within a slot formed in the medical instrument tray.

10. The apparatus for retaining medical instruments of claim 9, wherein the substantially rigid back plate is forcefully deformable from a substantially planar shape, whereby forceful deformation of the back plate facilitates insertion of the at least one tab into the at least one slot.

11. The apparatus for retaining medical instruments of claim 1, wherein the back plate further comprises at least one handle formed on the back plate, wherein the at least one handle extends from the back plate substantially perpendicularly relative to a middle portion of the back plate.

12. The apparatus for retaining medical instruments of claim 1, wherein the substantially rigid back plate has a curvature.

13. The apparatus for retaining medical instruments of claim 1, further comprising an outer case having an interior compartment, wherein the tray, the flexible grommet sheet, and the back plate are locatable within the interior compartment.

14. The apparatus for retaining medical instruments of claim 13, wherein the outer case further comprises:
   a base;
   a cover; and
   at least one fastener movably connected to one of the base and the cover, wherein the at least one fastener is movable between a locked position and an unlocked position.

15. The apparatus for retaining medical instruments of claim 14, wherein the at least one fastener is pivotally connected to the cover, and wherein, in the locked position, a distal end of the at least one fastener is biasedly engaged with a recessed portion of the base.

16. The apparatus for retaining medical instruments of claim 15, wherein the at least one fastener is pivotal on an axle, wherein the axle is connected between at least two portions of the cover.

17. The apparatus for retaining medical instruments of claim 16, wherein the at least one fastener further comprises a biased fastener, wherein the biased fastener includes at least one contact structure positioned to contact the recessed portion of the base when in the locked position.

18. A system for retaining a medical instrument comprising:
   a medical instrument tray having a substantially planar, rigid interior section and a plurality of sidewalls extending substantially perpendicularly from the interior section, wherein the interior section has a plurality of holes formed therein;
   an entirely flexible grommet sheet positioned abutting a first side of the medical instrument tray, the flexible grommet sheet comprising a flexible material formed into a substantially planar sheet having a plurality of openings therein, at least two openings of the plurality of openings acting in the manner of a grommet sized to receive a medical instrument, wherein at least a portion of the plurality of openings are substantially axially aligned with the plurality of holes formed within the interior section; and
   a substantially rigid back plate removably attached to the medical instrument tray, wherein the flexible grommet sheet is positioned between the first side of the interior section and the back plate, wherein the grommet sheet is tensionedly stretched across the back plate, and wherein the back plate has a plurality of holes positioned therein, wherein the plurality of holes are substantially axially aligned with the plurality of holes formed within the interior section.

19. A method of retaining medical instruments within a medical instrument container, the method comprising the steps of:
   positioning a flexible grommet sheet to abut a first side of a medical instrument tray, the flexible grommet sheet comprising a flexible material formed into a substantially planar sheet, the medical instrument tray having a substantially planar, rigid interior section, wherein the interior section has a plurality of holes formed therein, wherein the plurality of holes are substantially axially aligned with a plurality of openings within the flexible grommet sheet, wherein at least two openings of the plurality of openings act in the manner of a grommet sized to receive a medical instrument;
   removably attaching a substantially rigid back plate to the medical instrument tray, wherein the flexible grommet sheet is positioned between the first side of the medical instrument tray and the back plate, and wherein the back plate has a plurality of holes positioned therein, wherein the plurality of holes are substantially axially aligned with the plurality of holes formed within the medical instrument tray; and
   inserting a portion of the medical instrument through a substantially axially aligned set of at least one of the plurality of holes within the medical instrument tray, at least one of the plurality of openings within the flexible grommet sheet, and at least one of the plurality of holes within the back plate, whereby the medical instrument is retained at least partially by the flexible grommet sheet.

20. The method of claim 19, wherein at least one width dimension of an opening of the plurality of openings of the flexible grommet sheet is smaller than a diameter of a hole of the plurality of holes within the tray and the back plate.

* * * * *